United States Patent [19]

Wykypiel et al.

[11] Patent Number: 4,507,491

[45] Date of Patent: Mar. 26, 1985

[54] PROCESS FOR PREPARING 1-NITROBENZENE-2-ALKYLOXYCARBONYL-5-CARBOXYLIC ACIDS

[75] Inventors: Werner Wykypiel, Rodgau; Wolfgang Tronich, Eppstein, both of Fed. Rep. of Germany

[73] Assignee: Hoechst Aktiengesellschaft, Fed. Rep. of Germany

[21] Appl. No.: 445,008

[22] Filed: Nov. 29, 1982

[30] Foreign Application Priority Data

Dec. 8, 1981 [DE] Fed. Rep. of Germany ....... 3148422

[51] Int. Cl.$^3$ ........................ C07C 79/46; C07C 76/02
[52] U.S. Cl. .................................................. 560/020
[58] Field of Search .......................................... 560/20

[56] References Cited

FOREIGN PATENT DOCUMENTS 3001695  7/1981  Fed. Rep. of Germany ........ 560/20

OTHER PUBLICATIONS

Monick, Alcohols, Their Chemistry, Properties and Manufacture, (1968), 139.

*Primary Examiner*—Bernard Helfin
*Attorney, Agent, or Firm*—Connolly and Hutz

[57] ABSTRACT

To prepare a 1-nitrobenzene-2-alkyloxycarbonyl-5-carboxylic acid, a dialkyl benzene-1,4-dicarboxylate is first nitrated in a customary manner and the dialkyl 1-nitrobenzene-2,5-dicarboxylate compound obtained is subjected to a partial acidic ester hydrolysis without isolating the nitro compound prepared as an intermediate. The acidic ester hydrolysis is carried out in the presence of a catalytic amount of an organic solvent which is completely or partially miscible with water and has a boiling point of above 90° C. and/or of an emulsifier; it is preferably carried out at a temperature between 65° and 110° C.

6 Claims, No Drawings

PROCESS FOR PREPARING 1-NITROBENZENE-2-ALKYLOXYCARBONYL-5-CARBOXYLIC ACIDS

The invention relates to an improved process for preparing valuable intermediates for azo compounds, in particular pigments.

Czech Patent Specification No. 138,287 discloses a process for preparing 1-nitrobenzene-2-methoxycarbonyl-5-carboxylic acid. In this process, dimethyl benzene-1,4-dicarboxylate is nitrated in fuming sulfuric acid by means of a mixed acid of 20% strength oleum and 98% strength nitric acid; the dimethyl 1-nitrobenzene-2,5-dicarboxylate obtained is then first isolated and subsequently partially hydrolyzed by means of a large excess of 70% strength aqueous sulfuric acid. 1-Nitrobenzene-2-methoxycarbonyl-5-carboxylic acid precipitated in the acidic medium is then dissolved by means of sodium carbonate and reprecipitated by means of hydrochloric acid. In carrying out this process in industry, it suffers from the disadvantage that the waste water is very heavily polluted. The process moreover requires an additional isolating step as well as a purification operation, and it is impossible to prevent explosive dimethyl ether from forming from the methyl alcohol resulting in the hydrolysis of the ester group.

German Offenlegungsschrift No. 3,001,695 then proposed an improved acidic ester hydrolysis process in which, to avoid explosive dimethyl ether, said dialkyl ester of 1-nitrobenzene-2,5-dicarboxylic acid is hydrolyzed by means of aqueous nitric acid. However, on a large industrial scale this process also has certain defects, since in this case it is impossible to prevent a troublesome formation of nitrous gases.

The present invention now provides an improved process for preparing 1-nitrobenzene-2-alkyloxycarbonyl-5-carboxylic acid by means of which said disadvantages of these known processes are avoided.

The present invention relates to a process for preparing a 1-nitrobenzene-2-carbalkoxy-5-carboxylic acid in which one starts from a dialkyl ester of the benzene-1,4-dicarboxylic acid, nitrates this and then subjects the nitrated product to acidic ester hydrolysis, which comprises carrying out the acidic ester hydrolysis without intermediate isolation of the dialkyl ester of the 1-nitrobenzene-2,5-dicarboxylic acid from the nitration batch and in the presence of a catalytic amount of a solvent which is completely or partially miscible with water and has a boiling point above 90° C., and/or of an emulsifier.

The alkyl groups in the starting diester compounds and in the monoester final products are preferably alkyl groups having 1 to 4 carbon atoms, such as ethoxy groups and methoxy groups. The preparation of 1-nitrobenzene-2-methoxycarbonyl-5-carboxylic acid is preferable, in which, corresponding, the starting material used is the dimethyl ester of the benzene-1,4-dicarboxylic acid.

The benzene-1,4-dicarboxy-dialkyl ester can be nitrated in a manner which is known per se, such as, for example, by means of a sulfuric acid/nitric acid mixture or by means of 98 to 100% strength nitric acid, preferably in the presence of sulfuric acid, at a temperature of about 20° to 30° C. The partial acidic ester hydrolysis which follows the nitration reaction is carried out in an aqueous medium to which said catalytic amount of an organic solvent and/or of an emulsifier has been added. For this purpose, the nitration batch can be diluted with water or with dilute sulfuric acid after the nitration reaction has ended, preferably to a sulfuric acid content of about 60 to 85% by weight. The acidic hydrolysis is effected by means of the excess of the sulfuric acid/nitric acid mixture.

The organic solvent and/or the emulsifier used as the catalyst is added to the reaction batch in an amount of up to 6% by weight, for example 0.1 to 5% by weight, preferably 0.2 to 1% by weight, relative to the dialkyl benzene-1,4-dicarboxylate starting compound.

The acidic ester hydrolysis preferably takes place at a temperature above 60° C., such as, for example, at a temperature between 65° and 110° C., in particular between 75° and 95° C.

The process according to the invention can be carried out, for example, by first adding a sulfuric acid/nitric acid or oleum/nitric acid mixture of 98 to 100% strength nitric acid to the dialkyl benzene-1,4-dicarboxylate in 93 to 98% strength sulfuric acid and nitrating in this medium at a temperature between 15° and 35° C., then diluting the batch with water to an acid content of about 60 to 85% by weight, preferably 65 to 75% by weight, adding the organic solvent or the emulsifier or both and then carrying out the acidic ester hydrolysis at a temperature between about 80° and 90° C. When this hydrolysis has ended, the batch is cooled down to about 20° C. and diluted with cold water, and the 1-nitrobenzene-2-alkyloxycarbonyl-5-carboxylic acid precipitated is filtered off with suction, washed with water and dried.

Examples of organic solvents which are completely or partially miscible with water and which, according to the invention, may be added in a catalytic amount to the reaction batch and which have a boiling point of above 90° C. are alkanols, such as n-butanol, the hexanols, octanols, cyclohexanol, the divalent and trivalent aliphatic alcohols and their lower alkyl ethers, such as ethylene glycol, propylene glycol, diethylene glycol, dipropylene glycol, methyltrimethylene glycol, hexamethylene glycol, triethylene glycol, butane-1,4-diol, glycerol, diglycerol, ethylene glycol monomethyl ether, ethylene glycol monoethyl ether, diethylene glycol monomethyl ether, diethylene glycol monoethyl ether, diethylene glycol monopropyl ether, diethylene glycol monobutyl ether, triethylene glycol monopropyl ether, triethylene glycol monobutyl ether, 3-methoxybutanol, and also thiodiethylene glycol, γ-chloropropylene glycol, benzyl alcohol, phenoxyethanol, chlorophenoxyethanol, furfuryl alcohol, tetrahydrofurfuryl alcohol and cyclic aliphatic ethers, such as dioxane or tetrahydrofuran, and also esters of lower carboxylic acids with lower aliphatic alcohols, such as ethylene glycol acetate, methylglycol acetate, ethyl acetate, ethoxy butyrate, glycerol acetate, lower aliphatic ketones, such as acetone, methyl ethyl ketone, methyl isobutyl ketone or acetonylacetone, lower aliphatic monocarboxamides of primary or secondary aliphatic amines or of ammonia, such as formamide, dimethylformamide, acetamide, dimethylacetamide, N-methylacetamide or bis-β-hydroxyethylformamide, and also aliphatic hydroxy-ketones which are miscible with water, such as acetylcarbinol, propionylcarbinol, acetoin, acetyldimethylcarbinol, 1-hydroxy-3-acetylpropane, 1-hydroxy-4-acetylbutane, hydracetylacetone and, in particular, diacetone alcohol, and similarly nitriles of lower aliphatic carboxylic acids, such as acetonitrile, ethylenecyanohydrin, propylenecyanohydrin, chlorocyanohydrin, glyconitrile, lactonitrile, β-hydroxypropionitrile, ethoxyacetonitrile, β-methoxypropionitrile, β-ethoxypropionitrile, β-butoxypropionitrile or β-hydroxy-β-ethoxypropionitrile, and also aliphatic lactams, such as N-methylpyrrolidone, aliphatic lactones, such as butyrolactone, dialkyl sulfoxides, such as dimethyl sulfoxide, sulfolane, sulfolene, tetramethylene sulfone and bis-hydroxyethylene sulfone.

Examples of emulsifiers which, according to the invention, may be added in catalytic amounts to the reaction batch are anionic compounds having emulsifying properties, such as salts of $C_8$–$C_{18}$-fatty acids with alkali metals, such as sodium and potassium, or with metals of the 2nd or 3rd main group, such as calcium, magnesium and aluminum, of ammonia or of aliphatic amines, such as morpholine, triethanolamine, ethanolamine and isopropanolamine, salts of aliphatic sulfuric acid esters, such as Na-laurylsulfate, sodium salts of dialkyl sulfosuccinates, sulfuric acid esters of ethoxylated fatty alcohols and alkylphenols, Turkish Red, salts of aromatic sulfonic acids, such as alkylbenzenesulfonate, xylenesulfonates, naphthalenesulfonates and alkylnaphthalenesulfonates, and also polyphosphates and fatty acid addition products with hydrophilic groups, such as protein condensation products, and also cationic compounds having emulsifying properties, such as, for example, fatty amines, quaternary ammonium compounds, such as trimethylacetylammonium chloride, quaternary compounds of pyridine, of morpholine and of imidazoline, such as laurylpyridinium chloride, and also ampholytic compounds having emulsifying properties, such as long-chain substituted amino acids, for example N-alkyl-di-(aminoethyl)-glycine, N-alkyl-2-aminopropionate, betaines, such as (3-acylaminopropyl)-dimethylglycine and alkylimidazoliumbetaine, and also nonionic compounds having emulsifying properties, such as partial esters of polyalcohols, for example glycerol monostearate, distearate and oleates, sorbitol monostearate and monooleate, -and also ethylene oxide and propylene oxide adducts, for example to fatty acids, fatty alcohols or fatty amines (where these products can also have cationic properties) or to partial fatty acid esters of polyhydric alcohols, preferably of glycerol and of sorbitol, to alkylphenols, to water (polyalkylene glycols) and to amides of higher fatty acids, such as, for example, stearethanolamide, and also proteic substances having emulsifying properties and their degradation products having emulsifying properties, such as gelatin, albumins, sericin, sodium nucleinnates, zein and casein, and also synthetic high polymers having emulsifying properties, such as polyvinyl alcohol, polyvinylpyrrolidone and carboxyvinyl polymer.

Compared to known processes, the process according to the invention offers various advantages, such as, in particular, that it is no longer necessary to isolate from the nitration batch the nitro compound serving as an intermediate, that the degree of pollution of the waste water is reduced to a minimum and that the 1-nitrobenzene-2-alkyloxycarbonyl-5-carboxylic acid obtained as the final product is obtained in considerably improved yield and in a purity which is necessary, and adequate, to process this compound further to give the carbonyl chloride for the subsequent reaction to the corresponding carbonylarylamides (the 1-amino-2-carbalkoxy-5-carbox-arylamides obtainable from these 1-nitro-amide compounds by reduction, serve as diazo components in preparing valuable azo pigments; cf. German Patent Specification No. 1,263,202).

The examples which follow serve to illustrate the invention. Parts are parts by weight and percentages are percentages by weight unless otherwise stated.

EXAMPLE 1

297.5 parts of a mixture of 208.2 parts of 95% strength sulfuric acid and 89.3 parts of 100% strength nitric acid are added at a uniform rate within 2 hours with stirring and with slight external cooling to a solution of 250 parts of benzene-1,4-dicarboxylic acid dimethyl ester in 420 parts of 95% strength aqueous sulfuric acid at an internal temperature of 25° to 30° C. The nitration batch is then stirred for a further 4 hours at a temperature of about 15° to 25° C. (room temperature).

Without further external cooling 223 parts of water are then steadily added to this reaction mixture in the course of 15 minutes; during this period, the temperature rises to about 80° C., and this measure establishes a sulfuric acid concentration of about 70%. 0.5 part of ethylene glycol is added, and the reaction batch is stirred for a further 4 hours at 80° C. It is then cooled down to 20° C., 1,500 parts of water are stirred in, the mixture is stirred for a further 30 minutes, at 20° C., and the finely grained precipitated product is filtered off with suction, washed with about 4,000 parts of water until acid-free, and dried.

249 parts of 95% pure 1-nitrobenzene-2-methoxycarbonyl-5-carboxylic acid are obtained, which corresponds to 236.5 parts of a 100% pure product and hence to a yield of 81.6% of theory.

The same result is obtained when the nitrating mixture is forced over into a second vessel containing water and the hydrolysis is carried out after the sulfuric acid concentration required has been established.

COMPARATIVE EXAMPLE

Example 1 is repeated, except that the starting dimethyl 1-nitrobenzene-2,5-dicarboxylate compound is hydrolyzed without ethylene glycol. In this case, only a lumpy and impure material is obtained which cannot be filtered.

EXAMPLES 2 TO 14

Example 1 is repeated, except that an equivalent amount of one of the emulsifiers indicated in the tabled examples below or one of the solvents is used in a manner according to the invention instead of the ethylene glycol. A final product is obtained in similar good purity and yield. The values for the yields, converted to yields in percent of theory, are indicated in the tabled examples.

| Example | Catalyst used according to the invention | Yield (% of theory) |
|---|---|---|
| 2 | Reaction product of 19 moles of ethylene oxide with 1 mole of the addition product of bornane to p-cresol | 87.6 |
| 3 | Condensation product of 1 mole of orthophosphoric acid, of 1 mole of a reaction product of 2 moles of ethylene oxide with 1 mole of lauryl alcohol, and of 1 mole of a polyglycol (having an average molecular weight of 300) | 87.1 |
| 4 | Dodecyltrimethylammonium chloride | 87.1 |
| 5 | Stearyldimethylbenzylammonium chloride | 82.6 |
| 6 | Cetylpyridinium chloride | 81.5 |
| 7 | Condensation product of formaldehyde and naphthalenesulfonic acid (sodium | 79.6 |

-continued

| Example | Catalyst used according to the invention | Yield (% of theory) |
|---|---|---|
| | salt) | |
| 8 | Polyglycol having an average molecular weight of 200 | 82.5 |
| 9 | Polyglycol having an average molecular weight of 600 | 81.5 |
| 10 | Triethylene glycol | 84.8 |
| 11 | Dimethylformamide | 81.7 |
| 12 | Octyl alcohol | 81.7 |
| 13 | Dimethyl sulfoxide | 81.6 |
| 14 | Reaction product of 20 moles of ethylene oxide with 1 mole of oleyl alcohol | 82.1 |

We claim:

1. A process for preparing 1-nitro-benzene-2-alkoxy carbonyl-5-carboxylic acid from a dialkylester of benzene-1,4-dicarboxylic acid, comprising:
   nitrating, in a nitration medium containing a nitric acid/sulfuric acid mixture, the dialkyl ester of benzene-1,4-dicarboxylic acid to obtain a 1-nitro-2,5-dicarboxylic acid dialkyl ester intermediate,
   without isolation of said intermediate, diluting the nitration medium with an aqueous medium and adding a catalytic amount of a hydrolysis catalyst, said hydrolysis catalyst being an organic solvent which is at least partially miscible with water and has a boiling point above 90° C., an emulsifier, or a mixture thereof,
   partially hydrolyzing said intermediate to the 1-nitro-benzene-2-alkoxycarbonyl-5-carboxylic acid product in an acidic hydrolysis step by means of the excess of sulfuric acid/nitric acid mixture remaining in the diluted nitration medium, and recovering said product from said diluted nitration medium, said organic solvent being a divalent aliphatic alcohol or lower alkyl ether or lower carboxylic acid ester thereof, a cyclic aliphatic ether, a lower carboxylic acid ester of a lower aliphatic alcohol, a lower aliphatic ketone, or a lower monocarboxyamide of a primary or secondary aliphatic amine or of ammonia.

2. A process according to claim 1, wherein the amount of said hydrolysis catalyst added to the diluted nitration medium to obtain a hydrolysis medium is about 0.1 to about 5% by weight relative to the dialkyl benzene-1,4-dicarboxylate starting compound.

3. A process according to claim 1, wherein the amount of nitric acid in said nitration medium is approximately stoichiometric.

4. In a process for preparing a 1-nitrobenzene-2-alkoxycarbonyl-5-carboxylic acid by nitrating a dialkyl ester of the benzene-1,4-dicarboxylic acid and then subjecting the dialkyl ester of the 1-nitrobenzene-2-5-dicarboxylic acid to partial acidic ester hydrolysis, the improvement which comprises carrying out the acidic ester hydrolysis at a temperature between 65° and 110° C. without intermediate isolation of the dialkyl ester of the 1-nitrobenzene-2,5-dicarboxylic acid and in the presence of a catalytic amount of a hydrolysis catalyst, said hydrolysis catalyst being an organic solvent which is completely or partially miscible with water and has a boiling point of above 90° C., an emulsifier, or a mixture thereof, said catalytic amount being about 0.1 to about 5% by weight relative to the benzene-1,4-dicarboxylic acid dialkyl ester starting compound, and said organic solvent being a divalent aliphatic alcohol or lower alkyl ether or lower carboxylic acid ester thereof, a cyclic aliphatic ether, a lower carboxylic acid ester of a lower aliphatic alcohol, a lower aliphatic ketone, or a lower monocarboxyamide of a primary or secondary aliphatic amine or of ammonia.

5. The process according to claim 4, characterized in that the hydrolysis is carried out at a temperature between 75° and 95° C.

6. A process for preparing 1-nitrobenzene-2-alkoxycarbonyl-5-carboxylic acid from a dialkylester of benzene-1,4-dicarboxylic acid, comprising:
   nitrating, in a nitration medium containing a nitric acid/sulfuric acid mixture, the dialkyl ester of benzene-1,4-dicarboxylic acid to obtain a 1-nitro-2,5-dicarboxylic acid dialkyl ester intermediate,
   without isolation of said intermediate, diluting the nitration medium with an aqueous medium and adding a catalytic amount of a hydrolysis catalyst, said hydrolysis catalyst consisting essentially of ethylene glycol;
   partially hydrolyzing said intermediate to the 1-nitro-benzene-2-alkoxycarbonyl-5-carboxylic acid product in an acidic hydrolysis step by means of the excess of sulfuric acid/nitric acid mixture remaining in the diluted nitration medium, and recovering said product from said diluted nitration medium.

* * * * *